United States Patent
Zhao et al.

(10) Patent No.: US 8,061,224 B2
(45) Date of Patent: Nov. 22, 2011

(54) METHOD FOR PERFORMING A SHELF LIFETIME ACCELERATION TEST

(75) Inventors: Siping Zhao, Singapore (SG); Younan Hua, Singapore (SG); Ramesh Rao Nistala, Singapore (SG); Kun Li, Singapore (SG)

(73) Assignee: GLOBALFOUNDRIES Singapore Pte. Ltd., Singapore (SG)

( * ) Notice: Subject to any disclaimer, the term of this patent is extended or adjusted under 35 U.S.C. 154(b) by 535 days.

(21) Appl. No.: 12/115,550

(22) Filed: May 6, 2008

(65) Prior Publication Data

US 2009/0277287 A1    Nov. 12, 2009

(51) Int. Cl.
G01N 17/00    (2006.01)

(52) U.S. Cl. ............. 73/865.8; 73/86; 73/865.6; 73/866

(58) Field of Classification Search ................. 73/865.6, 73/865.8, 866, 86
See application file for complete search history.

(56) References Cited

U.S. PATENT DOCUMENTS

| | | | |
|---|---|---|---|
| 3,304,594 A * | 2/1967 | Madland ........................ | 438/11 |
| 4,091,919 A * | 5/1978 | MacLeod et al. ........... | 206/213.1 |
| 4,171,740 A * | 10/1979 | Clement et al. ............. | 206/213.1 |
| 5,352,328 A * | 10/1994 | Obeng et al. .................. | 438/691 |
| 5,576,223 A * | 11/1996 | Zeininger et al. ................. | 438/5 |
| 5,930,587 A * | 7/1999 | Ryan ............................... | 438/14 |
| 6,037,097 A * | 3/2000 | Bucchignano et al. .... | 430/270.1 |
| 6,511,923 B1 * | 1/2003 | Wang et al. .................... | 438/783 |
| 6,775,624 B2 * | 8/2004 | Storino ........................... | 702/34 |
| 6,969,638 B2 * | 11/2005 | Estepa et al. .................. | 438/115 |
| 2003/0104223 A1 * | 6/2003 | Ferm et al. ..................... | 428/447 |
| 2003/0194877 A1 * | 10/2003 | Yau et al. ....................... | 438/745 |
| 2004/0082174 A1 * | 4/2004 | Shieh et al. .................... | 438/689 |
| 2006/0024974 A1 * | 2/2006 | Azuri et al. .................... | 438/754 |
| 2007/0093069 A1 * | 4/2007 | Tsai et al. ...................... | 438/710 |

OTHER PUBLICATIONS

Picard et al., "Failure Mechanisms of Thin Silicon Tantalum Integrated Circuits (STIC) Resistors on Multi-Chip Modul (MCM)", 31st Annual Proceedings of the Reliability Physics Symposium, Mar. 1993.*
John W. Osenbach, "Corrosion-Induced Degradation of Microelectronic Devices", Semiconductor Science Technology, vol. 11, 1996, pp. 155-162.*
Shive et al., "Investigating the Formation of Time-Dependent Haze on Stored Wafers", Mico Magazine, Mar. 2001.*
Soden et al., "W88 Integrated Circuit Shelf Life Program", Sandia National Laboratories, Jan. 1998.*

* cited by examiner

*Primary Examiner* — David A. Rogers
(74) *Attorney, Agent, or Firm* — Horizon IP Pte Ltd

(57) ABSTRACT

Embodiments of the invention provide a method of determining a storage lifetime of a wafer in a storage environment, the storage environment corresponding to an environment having a first value of temperature and a first value of relative humidity, the wafer having a pre-test value of a first contamination parameter, including the steps of: subjecting the wafer to a test environment for a test period, the test environment includes an environment having a second value of temperature and a second value of relative humidity; subsequently, inspecting the wafer thereby to determine a post-test value of a second contamination parameter, wherein the second value of relative humidity is greater than 30% and the second value of wafer temperature is greater than 30° C.

20 Claims, 3 Drawing Sheets

|        | RH=55%   | RH=70%   | RH=85%   |
|--------|----------|----------|----------|
| 55°C   | 72.5 hrs | 35.5 hrs | 19.6 hrs |
| 65°C   | 34.8 hrs | 16.9 hrs | 9.5 hrs  |
| 75°C   | 17.5 hrs | 8.5 hrs  | 4.7 hrs  |

Fig. 1

METHOD FOR PERFORMING A SHELF LIFETIME ACCELERATION TEST

FIELD OF THE INVENTION

The present invention relates to a method for performing shelf lifetime acceleration testing of integrated circuit (IC) wafers. In particular, but not exclusively, embodiments of the invention relate to a method of accelerating the testing of the shelf lifetime of an IC wafer by reference to the condition of bondpads of the IC.

BACKGROUND OF THE INVENTION

Integrated circuits typically comprise a large number of active and passive electronic devices formed on a single semiconductor wafer. Electrical connections (or 'bonds') between the wafer and external electrodes of (say) a wafer package are typically made by bonding 'bondwires' to 'bondpads' provided on the wafer.

The problem exists that the surface of a bondpad can become contaminated. If the amount of contamination exceeds a critical value, bonds formed between a bondwire and a bondpad may be unreliable and susceptible to breakage. In some cases, if the amount of contamination is excessive, it may be difficult to form a bond between a bondwire and a bondpad.

Bondpads are typically formed from a metallic material such as aluminum. Contamination of the surface of an aluminum bondpad by fluorine (F) can result in the formation of aluminum-fluoride-oxide ($Al_xF_yO_z$) due to reaction between fluorine, aluminum, oxygen and moisture over time. During storage of the wafer, the amount of $Al_xF_yO_z$ can increase until the formation of reliable bonds to a bondpad is no longer possible.

It is known to attempt to determine a shelf lifetime of a wafer provided with bondpads in order to reduce a failure rate of packaged integrated circuits by performing a 'shelf lifetime test'. The shelf lifetime of a wafer is the length of time for which the wafer may be stored under suitable, predetermined storage conditions before its condition is no longer acceptable for subsequent IC fabrication.

Knowledge of the shelf lifetime is important because it enables IC manufacturers to reduce the number of IC devices of inferior quality. It also enables wafer suppliers to provide a warranty or guidance to a manufacturer in respect of the shelf lifetime of a wafer.

The traditional 'shelf lifetime test' involves the steps of placing a wafer from a given batch of wafers in a wafer box that has a small amount of deionised (DI) water in a lower portion of the box. The wafer box is closed and stored at room temperature for a predetermined period of time. The selected wafer is known as the 'test wafer'.

The test wafer is inspected after a test period corresponding to an effective storage period under normal storage conditions of one year (or any other required period of time) from the date of fabrication of the bondpads. An amount of contamination on the bondpads of the test wafer is determined; this determination may be made by reference to one or more bondpads of the test wafer.

If the bondpads of the test wafer are found to have a contamination level below a critical contamination level for bond formation, the batch of wafers from which the test wafer was taken may be considered suitable for storage for a predetermined time, for example one year from the date of fabrication of the bondpads as discussed above.

If the bondpads of the test wafer are found to have a contamination level equal to or above the critical contamination level for bond formation, measures may be taken to reject the batch of wafers from which the test wafer was taken. Such wafers might then be discarded, or subjected to a cleaning process before subsequent bond formation.

Empirical results suggest that, in order to simulate a storage period of 1 year under normal storage conditions by means of the test described above, a period of testing of from about 23 to about 198 days is required. This period is calculated assuming that the wafer is stored at a temperature of 22° C. in an environment having a relative humidity of 75%.

The test period of 23 to about 198 days is excessive in the context of IC fabrication. The requirement to perform a shelf lifetime test on a test wafer of a batch of wafers before shipping the batch to a customer introduces a significant delay in the delivery of the batch.

Furthermore, the results of the traditional test are found to be unrepeatable in a reliable manner. This introduces a level of uncertainty in the determination whether a given batch of wafers may be warrantied as suitable for being stored for a give period of time.

SUMMARY OF THE INVENTION

It is an aim of embodiments of the invention to at least partially mitigate at least some of the above mentioned problems.

It is an aim of embodiments of the invention to provide an improved test method and apparatus for determining a shelf lifetime of an IC wafer.

Another aim of embodiments of the invention is to provide a test method for determining a shelf lifetime of an IC wafer such that the test method has a reduced number of artefacts associated therewith.

A still further aim of embodiments of the invention is to provide an improved test method for determining a shelf lifetime of an IC wafer capable of providing a determination of shelf lifetime in a shorter period of time than that of the traditional test method.

According to a first aspect of the invention there is provided a method of determining a storage lifetime of a wafer in a storage environment, said storage environment corresponding to an environment having a first value of temperature and a first value of relative humidity, said wafer having a pre-test value of a first contamination parameter, comprising the steps of: subjecting the wafer to a test environment for a test period, said test environment comprising an environment having a second value of temperature and a second value of relative humidity; subsequently, inspecting said wafer thereby to determine a post-test value of a second contamination parameter, wherein said second value of relative humidity is greater than 30% and said second value of wafer temperature is greater than 30° C.

According to a second aspect of the invention there is provided a method of determining a storage lifetime of a wafer in a storage environment, said storage environment corresponding to an environment having a first value of temperature and a first value of relative humidity, said wafer having a pre-test value of a first contamination parameter, comprising the steps of: subjecting the wafer to a test environment for a test period, said test environment comprising an environment having a second value of temperature and a second value of relative humidity; subsequently inspecting said wafer thereby to determine a post-test value of a second contamination parameter, wherein said second value of relative humidity is greater than 30% and said second value of wafer temperature is greater than 30° C.; and determining whether or not said post-test value of said second contamination parameter exceeds a critical value of said second contamination parameter, whereby said second contamination parameter corresponds to a second contamination parameter of a bondpad, said critical value of said second contamination parameter corresponds to an amount of contamination of a bondpad indicative of a bondpad that is unsuitable for bonding to a bondwire, and said second value of relative humidity and said second value of temperature are selected to provide dewing-free conditions.

According to a third aspect of the invention there is provided a method of determining a storage lifetime of a second wafer having a first value of a first contamination parameter, comprising the steps of: subjecting a first wafer to a first test environment for a first time period, said first test environment comprising an environment having a first value of temperature and a first value of relative humidity, said first wafer having a pre-test value of said first contamination parameter corresponding to said first value of said first contamination parameter of said second wafer; subsequently inspecting said first wafer thereby to determine a post-test value of a second contamination parameter, whereby said first value of relative humidity is greater than 30% and said first value of wafer temperature is greater than 30° C.; subsequently calculating a value of a second time period over which said second wafer would develop a value of said second contamination parameter corresponding to said post-test value of said second contamination parameter of said first wafer, when said second wafer is subjected to a second environment, said second environment comprising an environment having a second value of temperature and a second value of relative humidity.

Embodiments of the invention have the advantage that the time period required in order to perform a shelf lifetime acceleration test may be significantly reduced. This is at least in part due to the fact that a wafer is heated above a normal storage temperature during the course of the test, thereby accelerating a rate of formation of contamination. In prior art tests, a wafer is not heated during the course of a test.

The inventors' investigations have revealed that some traditional test methodologies are fundamentally flawed. This is because, under certain test conditions, the presence of water droplets on a wafer during the test can affect the formation of fluorine-induced corrosion defects on the surface of one or more bondpads.

Embodiments of the invention have the advantage of avoiding introduction of artefacts. This is because dewing-free conditions are maintained during the course of a test according to embodiments of the invention. By maintaining dewing-free conditions, the formation of water droplets on the surface of the wafer is avoided.

BRIEF DESCRIPTION OF THE DRAWINGS

Embodiments of the present invention will now be described hereinafter, by way of example only with reference to the accompanying drawings, in which:

FIG. 1 shows a table of values of a required testing time in a shelf lifetime acceleration test (SLAT) according to an embodiment of the invention as a function of wafer temperature and relative humidity, the test being configured to simulate a storage period of 1 year under normal storage conditions.

DETAILED DESCRIPTION OF THE INVENTION

Figure 2:
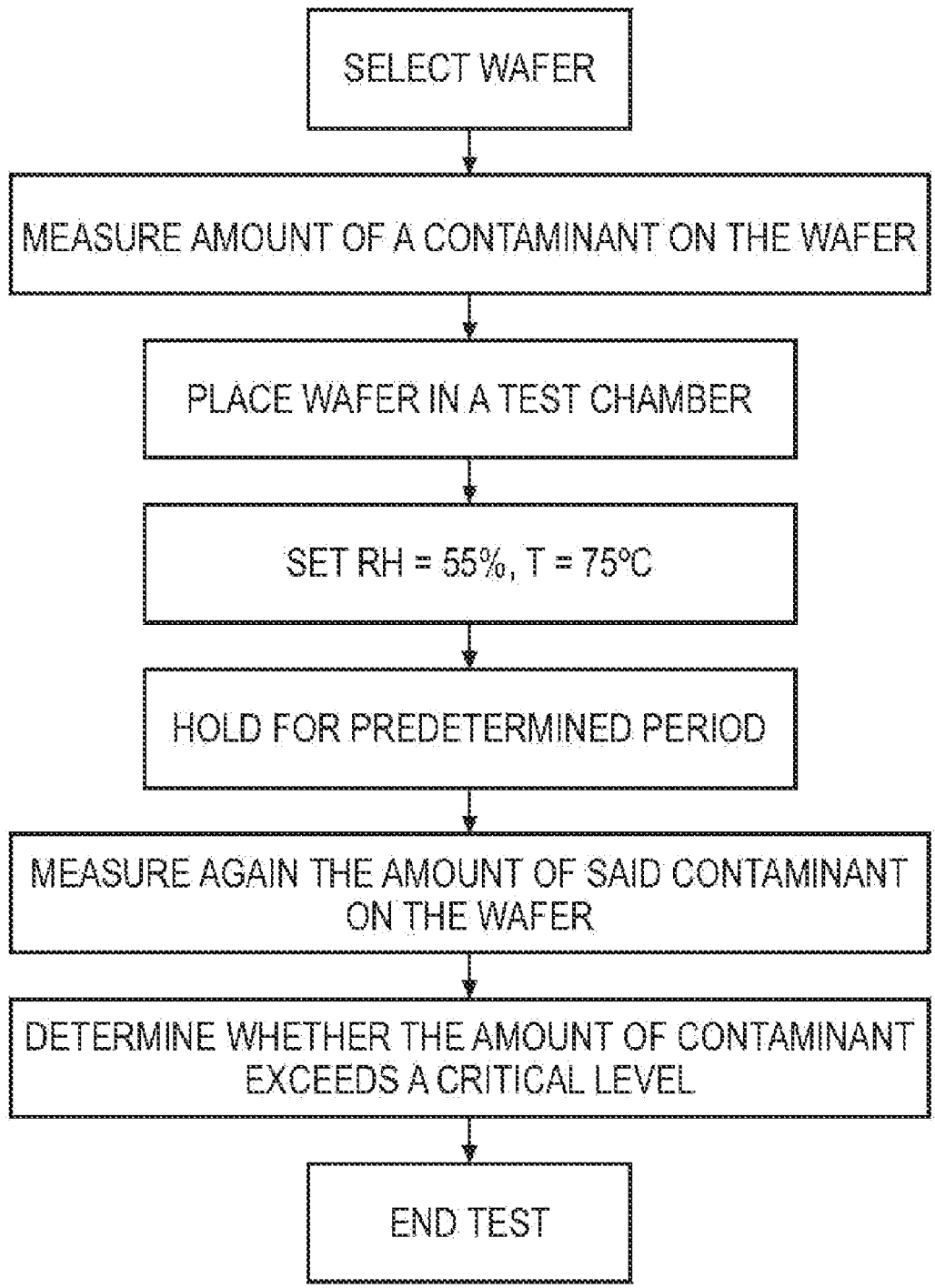
FIG. 2 shows a flow diagram of a process of testing a wafer according to a first embodiment of the invention.

The following embodiments are intended to illustrate the invention more fully without limiting its scope, since numerous modifications and variations will be apparent to those skilled in the art.

The present inventors have sought to develop a new electrochemical model for the determination of shelf lifetime of a wafer. The methodology is embodied in a new shelf lifetime acceleration test (SLAT) proposed herein.

It has been understood by the present inventors that oxygen ($O_2$) and water ($H_2O$) enhance fluorine-induced corrosion and galvanic corrosion of aluminum bondpads on semiconductor wafers during wafer storage.

Fluorine induced corrosion is believed to proceed according to the following reaction schemes:

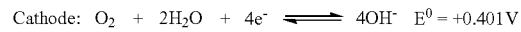

where $E^0$ is the redox potential of the indicated chemical reaction.

Subsequently, the reaction products react according to the scheme:

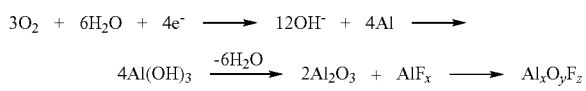

During the course of the SLAT, aluminum oxide fluoride ($Al_xO_yF_z$) forms on aluminum bondpads of a wafer having fluorine contamination. The $Al_xO_yF_z$ is in the form of small islands. As viewed in a scanning electron microscope (SEM) the defects appear as white particles or 'white dots' on the bondpads, depending upon the imaging conditions used. Such defects are therefore sometimes referred to as 'white-dot defects'.

The presence of increased moisture ($H_2O$) results in an increase in the rate of reaction of aluminum and fluorine to form $Al_xO_yF_z$. Similarly, increased temperatures also result in an increase in the rate of reaction.

Acceleration of the rate of reaction may be modelled using the Hallberg-Peck model. The model may be stated as follows:

$$AF = (AF, H) \times (AF, T) \quad (1)$$

where AF is an acceleration factor of the overall reaction process described above; (AF, H) is the acceleration factor of the reaction due to humidity; and (AF, T) is the acceleration factor due to temperature.

Using the Hallberg-Peck relationship:

$$AF = \left(\frac{RH_u}{RH_t}\right)^{-n} \times \left(\frac{E_a}{k}\right) \cdot \left(\frac{1}{T_u} - \frac{1}{T_t}\right) \quad (2)$$

where $E_a$ is an activation energy for fluorine-induced corrosion of an aluminum bondpad surface, n is an exponential constant, k is Boltzmann's constant, $T_u$ is the temperature of the wafer during normal storage, $RH_u$ is the relative humidity of the normal storage environment, $T_t$ is the temperature of the wafer in the testing environment and $RH_t$ is the relative humidity of the testing environment.

Investigations of defect structures formed during the course of the inventors' investigations revealed that the presence of water droplets on a wafer during testing resulted in the introduction of an artificially high density of defects that may not necessarily be responsible for fluorine-induced corrosion.

The inventors determined that in order to prevent the formation of artefacts, the formation of water droplets on the wafer surface should be avoided. The SLAT tests should therefore be performed under conditions that avoid the formation of water droplets, i.e. under 'dewing-free' conditions.

The inventors have determined that dewing-free conditions may be obtained under the following conditions: $RH_t < 85\%$; and $T_t < 75°$ C. Other values of relative humidity and temperature of the test environment are also useful.

The remaining parameters to be used in the wafer fabrication environment have been determined as follows:
$E_a = 0.7$ eV
$n = 3$
$k = 8.617 \times 10^{-5}$ eV
$T_u = 22°$ C.
$RH_u = 28\%$
Other values of $T_u$ and $RH_u$ are also useful.

Inserting these values into equation (2), and requiring a simulated shelf lifetime of 1 year under test conditions whereby $RH_t = 55\%$ and $T_t = 75°$ C., we obtain an overall acceleration factor AF=502. Thus, in order to obtain a simulated shelf lifetime of 1 year, a SLAT test under these conditions for a period of 17.5 hours is required. Clearly, this is a considerably shorter period than that required for the traditional test.

FIG. 1 is a table of values of SLAT testing times required to simulate a storage period of 1 year as a function of $RH_t$ (%) and $T_t$ (° C.). It can be seen from the table that if a SLAT test is performed at a value of $RH_t$ of 85%, and a temperature of 75° C., the test would take only 4.7 hours. In contrast, if the SLAT test were performed at a value of $RH_t$ of 55%, and a temperature of 55° C., the test would take about 72.5 hours.

This is in contrast to the traditional lifetime test, which requires a period of between 23 days and 198 days. Thus, embodiments of the present invention enable a considerable reduction in the time required to perform a shelf lifetime test. Furthermore, embodiments of the invention have the advantage of reducing a level of artefacts associated with the traditional shelf lifetime test. This has the advantage of increasing a reliability of the test.

It will be appreciated that simulating a storage period of other than 1 year is also useful. Furthermore, values of $RH_t$ and $T_t$ other than those listed in the table are also useful.

FIG. 2. shows a flow diagram of a sequence of steps for the performance of a SLAT test according to a first embodiment of the invention. SLAT tests according to the first embodiment have been performed using a temperature and humidity controlled test chamber (Taichy HRM-80FA). The tests were performed over the temperature range from room temperature to 100° C., and at values of relative humidity from 30-95%.

The SLAT test sequence according to the first embodiment begins with the selection of a wafer to be tested from a batch of wafers. The wafer is then inspected to determine an amount of contaminant present on one or more bondpads of the wafer.

According to the first embodiment, the wafer is subjected to Auger electron spectroscopy examination (AES) in order to determine a level of fluorine (F) contamination. In some embodiments the wafer is also subjected to SEM inspection to identify whether or not so-called white-dot defects are present. If white-dot defects are present, the number density of white-dot defects may be determined by inspection of an SEM image.

In some embodiments of the invention a thickness of any aluminum oxide or aluminum fluoride oxide is determined. In embodiments of the invention the thickness is determined using transmission electron microscopy (TEM).

The wafer to be tested is then mounted in a quartz holder and placed inside the test chamber. According to the present embodiment the quartz holder is of a size in the range from 6" to 12" (0.15240 m-0.30480 m). The test chamber environment is set to a predetermined temperature and relative humidity for a predetermined time period.

According to the present embodiment the test chamber environment is set to a temperature of 75° C. and a relative humidity of 55% for a period of 17.5 hours. In some embodiments of the invention the temperature and/or relative humidity are set to other values, for the same or a different period of time.

FIG. 1 is a table of test times as a function of test temperature and test relative humidity in order to simulate a storage period of one year. It will be appreciated that longer or shorter test times may be used to simulate a longer or shorter storage period. Similarly, the values of temperature and relative humidity may be varied in order to simulate similar or different test periods, according to a user's requirement.

The values of temperature and relative humidity shown in FIG. 1 are determined according to a requirement to maintain dewing-free conditions within the test chamber. That is, the formation of water droplets on the wafer within the chamber is avoided when a test environment is used according to the values presented in FIG. 1. It will be appreciated that dewing free conditions may also be obtained using other combinations of values of temperature and relative humidity.

Once the test period has ended, the wafer is removed from the test chamber. In some embodiments of the invention the test environment is returned to ambient conditions in a controlled manner before removal of the wafer, in order to avoid the formation of water droplets on the wafer. In other words, dewing free conditions are maintained after the test has been terminated. According to the first embodiment of the invention, dewing free conditions are maintained until post-test inspection of the wafer is complete.

Following removal of the wafer from the test environment, the wafer is subjected to post-test inspection. According to the present embodiment the post-test inspection is performed using SEM to determine a number density of white-dot defects.

If SEM inspection of a bondpad indicates that the number density of white-dot defects on the bondpad is below a critical level, the bondpad is deemed to be a bondpad capable of sufficiently reliable bonding to a bondwire to be used in IC fabrication. The critical level of white-dot defects below which a bondpad is capable of sufficiently reliable bonding is determined empirically.

In some embodiments of the invention, a determination of an amount of fluorine present on the wafer surface is performed following removal of the wafer from the test environment. In some embodiments of the invention the determination of an amount of fluorine is made using AES.

It will be appreciated that in some embodiments of the invention, a determination of the amount of white-dot defects is made by alternative inspection means, such as by using a scanned probe microscope or a transmission electron microscope. Other apparatus and methods are also useful. Similarly, in some embodiments of the invention, a determination of an amount of fluorine present on the wafer surface is made using a tool other than AES.

In a second embodiment of the invention, a SLAT test is used to determine a maximum storage lifetime of a wafer.

Figure 3:
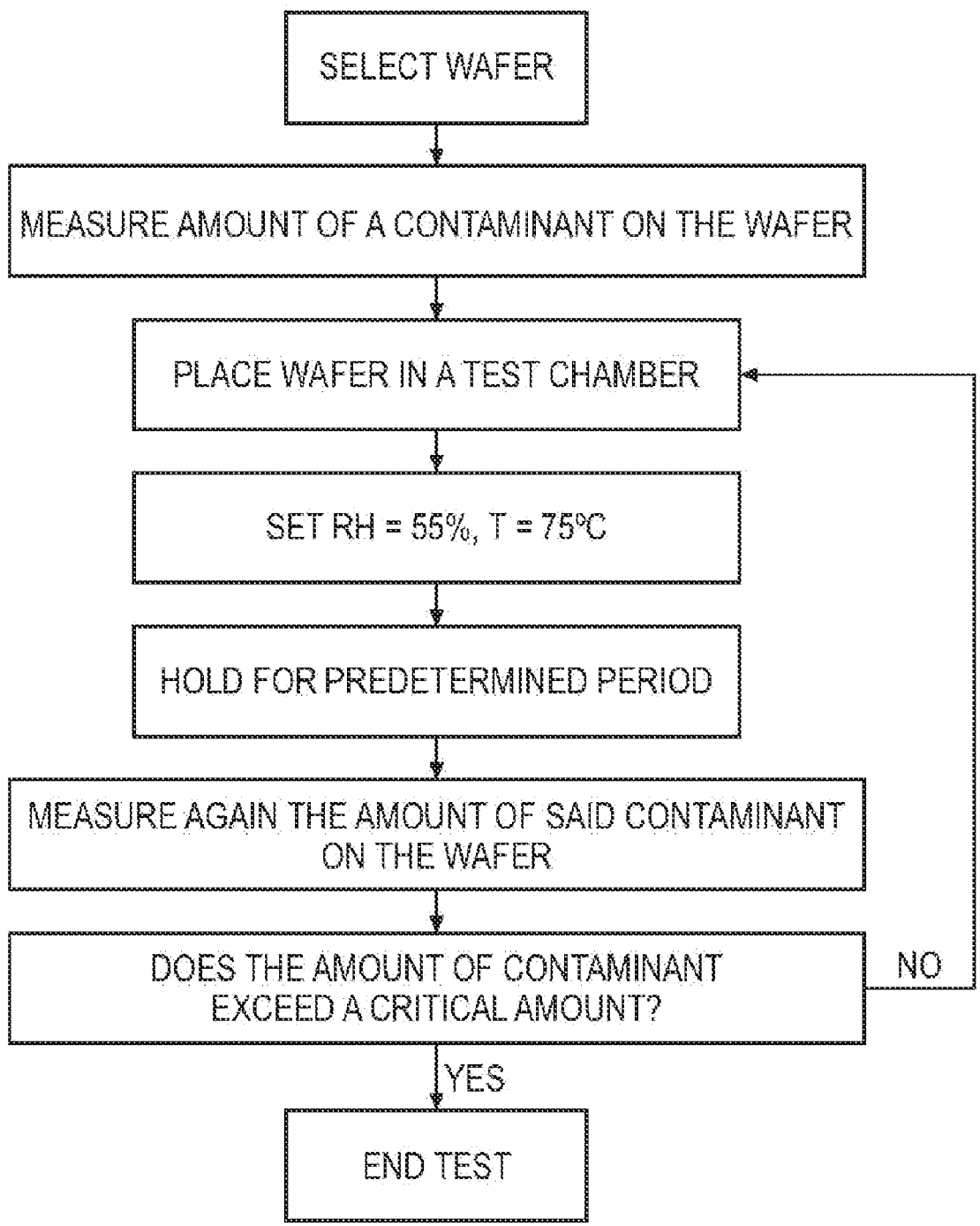
FIG. 3 shows a flow diagram of a process of testing a wafer according to a second embodiment of the invention.

FIG. 3. shows a flow diagram of a sequence of steps for the performance of a SLAT test according to the second embodiment.

As in the case of the first embodiment, the sequence of steps comprising the test begins with the selection of a wafer to be tested from a batch of wafers. The wafer is inspected to determine an amount of contaminants present on the wafer.

According to the second embodiment, the wafer is subjected to Auger electron spectroscopy examination (AES) in order to determine a level of fluorine (F) contamination. Other methods of determining a level of fluorine contamination are also useful.

It will be appreciated that the wafer may also be subjected to SEM inspection to identify whether or not so-called white-dot defects are present. If white-dot defects are present, the number density of white-dot defects may be determined by inspection of an SEM image.

A thickness of a layer of any aluminum oxide or aluminum fluoride oxide present on one or more bondpads of the wafer surface may also be determined. In embodiments of the invention the thickness is determined using transmission electron microscopy (TEM). Other methods of determining thickness of layers are also useful.

The wafer to be tested is then placed in a quartz holder and inserted into the test chamber. The test chamber environment is set to a predetermined temperature and relative humidity for a predetermined time period.

According to the second embodiment the test chamber environment is set to a temperature of 75° C. and a relative humidity of 55% for a predetermined initial test period. Once the predetermined period has expired, the wafer is removed from the test chamber. It will be appreciated that other values of temperature and relative humidity are useful.

The table of test times as a function of test temperature and test relative humidity shown in FIG. 1 may be used to determine the initial test period. It will be appreciated that longer or shorter initial test periods may be used. Similarly, the values of temperature and relative humidity for the initial test period may be changed, according to a user's requirement.

The values of temperature and relative humidity shown in FIG. 2 are determined according to a requirement to maintain dewing-free conditions within the test chamber. That is, the formation of water droplets on the wafer within the chamber is avoided when a test environment is used according to the values of temperature and relative humidity presented in FIG. 2.

It will be appreciated that other combinations of temperature and relative humidity are useful in order to maintain dewing free conditions.

Once the initial test period has ended, the wafer is removed from the test chamber. In some embodiments of the invention the test environment is returned to ambient conditions before removal of the wafer, in a controlled manner, in order to avoid the formation of water droplets on the wafer. In other words, dewing free conditions are maintained after the test has been terminated.

Following removal of the wafer from the test environment, the wafer is subjected to post-test inspection. According to the second embodiment the post-test inspection is performed using SEM to determine a number density of white-dot defects on a selected one or more bondpads of the wafer. If the number density of white-dot defects on the one or more bondpads is below a critical level, the wafer is deemed to be a wafer having bondpads capable of sufficiently reliable bonding to a bondwire. The critical level of white-dot defects below which a bond pad is capable of sufficiently reliable bonding is determined empirically.

According to some embodiments of the invention dewing free conditions are maintained until post-test inspection of the wafer is complete.

In some embodiments of the invention, a determination of an amount of fluorine present on the bondpads is performed following removal of the wafer from the test environment. In some embodiments of the invention the determination of an amount of fluorine is made using AES.

It will be appreciated that in some embodiments of the invention, a determination of the amount of white-dot defects on one or more bondpads is made by alternative inspection means, such as using a scanned probe microscope, a transmission electron microscope, or any other suitable means. Similarly, in some embodiments of the invention, a determination of an amount of fluorine present on the bondpads is made using a tool other than AES.

In some embodiments of the invention SEM inspection of white-dot defects is performed at a magnification of 50 k. Alternatively or in addition SEM inspection may be performed at a magnification of 100 k. Other values of magnification are also useful.

If the wafer is deemed to be a wafer having bondpads capable of sufficiently reliable bonding to a bondwire, the wafer is returned to the test chamber for a further period of time. According to the present invention, the initial test period is 17.5 hours and the further period of time is 1.0 hour, at a temperature of 75° C. and a relative humidity of 55%. Other values of the initial test period and of the further period of time are also useful.

The process of removal and inspection of the wafer is repeated when the further period has expired, as per the process following expiry of the initial test period. If the wafer is again determined to be a wafer having bondpads capable of sufficiently reliable bonding to a bond wire, the wafer may be returned to the test chamber for a further period of time. The effective storage period of the wafer under the test conditions used is determined based on the cumulative time period spent under a given set of test conditions.

If the wafer is determined not to be a wafer capable of sufficiently reliable bonding to a bondwire, then the storage period for which a wafer with bondpads is deemed to be capable of sufficiently reliable bonding to a bondwire is that corresponding to the length of the longest test period for which the wafer was deemed to be capable of sufficiently reliable bonding to a bondwire. If no such storage period was determined, due to an amount of contamination exceeding a critical level following the initial test period, then the storage period for which the wafer may be stored whilst remaining capable of sufficiently reliable bonding to a bondwire is determined to be less than the period corresponding to the initial test period of the wafer.

It will be appreciated that in some embodiments of the invention the kind of defect and the characteristic of a given defect that is used to determine whether or not a bondpad of a wafer is capable of sufficiently reliable bonding to a bondwire may be other than a measure of the number density of white-dot defects. For example, a defect other than a white-dot defect may be used. Similarly, a characteristic of a defect other than a number density of a given defect may be used. For example, a size of a given defect, such as an average size (a mean, median or mode average), a shape, a thickness of a layer, a volume, or any other suitable characteristic may be used.

It will be appreciated that some embodiments of the invention allow a control limit (CL) and a specification limit (SL) of fluorine contamination of a wafer to be established. CL is a measure of process capability and variations thereof, and is generally taken to be ±3σ (where σ is the standard deviation). SL, on the other hand, defines upper and lower bounds of the functionality of a process.

According to some embodiments, the limit of fluorine contamination on bondpads of a wafer before a wafer becomes unsuitable for storage for a required time period is determined.

Knowledge of this limit of contamination is useful. This is because, if it is determined that the fluorine contamination level of a wafer before a SLAT test exceeds a certain critical level of fluorine contamination, it may be predicted that the wafer will most likely fail the SLAT test. In other words, the number of white-dot defects on bondpads of that wafer following a SLAT test will exceed a critical density of white-dot defects to allow reliable bonding, making it impossible to form a sufficiently reliable bond to that bondpad without remedial action such as cleaning of the bondpad to remove the white-dot defects.

Determination of the limiting value of fluorine contamination corresponding to a wafer that is suitable for storage for a required time period may be made as follows.

A series of wafers having different levels of fluorine contamination are subjected to a SLAT test according to the first embodiment of the invention under identical conditions. A wafer passing the SLAT test with the highest amount of fluorine contamination before the SLAT test was performed is then identified. The critical amount of fluorine contamination for reliable bond formation is then determined to correspond to the amount of fluorine contamination of this wafer before the SLAT test was performed.

Other methods of determining the storage lifetime of a wafer are also useful.

It will be appreciated that in alternative embodiments of the invention, initial contaminants other than fluorine may be used to provide a corresponding control limit and/or specification limit. A knowledge of an amount of initial contaminant other than fluorine is useful in determining a shelf lifetime of a wafer, in addition to or instead of an amount of fluorine.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. A method of fabricating an IC comprising:
providing a batch of wafers comprising the IC which has been partially processed;
testing a test wafer of the batch of wafers to determine if the batch of wafers comprises a desired shelf life, wherein the testing comprises
determining an acceleration factor based on first and second test parameters and first and second storage parameters,
calculating a test time from the acceleration factor which corresponds to the desired shelf life, and
testing the test wafer in a first test environment with the first and second test parameters for a test period equal to at least the test time;
determining a post-test value of a contamination parameter of the test wafer,
wherein the post-test contamination parameter comprises a post-test value of a second contamination parameter of the test wafer; and
if the test wafer comprises the desired shelf life, storing the batch of wafers for a period of time equal to or less than the desired shelf life before continuing to process the wafers to complete forming the IC.

2. The method of claim 1 wherein the first and second test parameters are selected to provide dewing-free conditions.

3. The method of claim 1 wherein the post-test value of the second contamination parameter corresponds to a value above which the wafer must be rejected.

4. The method of claim 1 wherein the post-test value of the second contamination parameter corresponds to an amount of a second contaminant.

5. The method of claim 4 wherein the second contaminant comprises $Al_xO_yF_z$.

6. The method of claim 1 further comprises:
subjecting the wafer to a second test environment for a further test period, the second test environment comprising an environment having a second test temperature and a second test relative humidity; and
determining a further post-test value of the second contamination parameter.

7. The method of claim 6 further comprises determining whether or not the further post-test value of the second contamination parameter exceeds a critical value of the second contamination parameter.

8. The method of claim 1 wherein the first and second test parameters comprise a first test temperature and a first test relative humidity.

9. The method of claim 8 wherein the first and second storage parameters comprise a first storage temperature and a first storage relative humidity.

10. The method of claim 9 further comprises determining a pre-test value of a first contamination parameter of the test wafer.

11. The method of claim 1 further comprises determining a pre-test value of a first contamination parameter of the test wafer.

12. The method of claim 11 wherein the pre-test value of the first contamination parameter corresponds to an amount of a first contaminant.

13. The method of claim 12 wherein the first contaminant comprises $Al_xO_yF_z$.

14. The method of claim 1 further comprises determining whether or not the post-test value of the second contamination parameter exceeds a critical value of the second contamination parameter.

15. The method of claim 14 wherein the first and second contamination parameters correspond to first and second contamination parameters of a bondpad.

16. The method of claim 15 wherein the critical value of the second contamination parameter corresponds to an amount of contamination of a bondpad indicative of a bondpad that is unsuitable for bonding to a bondwire.

17. A method of fabricating a device comprising:
  providing a plurality of wafers comprising partially processed devices;
  testing a test wafer of the plurality of wafers to determine if the wafers comprise a desired shelf life, wherein testing comprises
    determining an acceleration factor based on a first set of test parameters and a first set of storage parameters,
    calculating a test time from the acceleration factor which corresponds to the desired shelf life, and
    testing the test wafer in a first test environment with the first set of test parameters for a test period equal to at least the test time;
    determining a pre-test value of a first contamination parameter and a post-test value of a second contamination parameter of the test wafer; and
  if the test wafer comprises the desired shelf life, storing the plurality of processed wafers for a period of time equal to or less than the desired shelf life before continuing processing the wafers to complete forming the devices.

18. The method of claim 17 wherein the acceleration factor is about 502.

19. The method of claim 18 further comprises:
  subjecting the wafer to a second test environment for a further test period, the second test environment comprising an environment having a second set of test parameters;
  determining a further post-test value of the second contamination parameter; and
  determining whether or not the further post-test value of the second contamination parameter exceeds a critical value of the second contamination parameter.

20. A method of fabricating a device comprising:
  providing a plurality of wafers comprising the devices which has been partially processed;
  testing a test wafer from the plurality of wafers to determine an effective shelf life of the batch of wafers, wherein the testing comprises
    determining an acceleration factor based on a first set of test parameters and a first set of storage parameters,
    calculating a test time from the acceleration factor,
    testing the test wafer in a first test environment with the first set of test parameters for a test period equal to the test time,
    determining a post-test value of a contamination parameter,
    repeating the testing of the test wafer by subjecting the test wafer to further test environments with further sets of test parameters for further test periods until the post-test value of the contamination parameter exceeds a critical value of the contamination parameter, and
    determining the effective shelf life based on the test periods; and
  storing the plurality of wafers for a period of time equal to or less than the effective shelf life before continuing to process the wafers to complete forming the devices.

* * * * *